United States Patent
Hermansson et al.

(10) Patent No.: US 10,561,538 B2
(45) Date of Patent: *Feb. 18, 2020

(54) METHOD FOR PRODUCTION OF DISPOSABLE ABSORBENT ARTICLES

(71) Applicant: SCA Hygiene Products AB, Göteborg (SE)

(72) Inventors: Kent Hermansson, Västra Frölunda (SE); Jan Wästlund-Karlsson, Mölndal (SE); Margareta Wennerbäck, Mölnlycke (SE); Carina Hedlund, Mölnlycke (SE); Niclas Norrby, Göteborg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 43 days.

This patent is subject to a terminal disclaimer.

(21) Appl. No.: 15/898,803

(22) Filed: Feb. 19, 2018

(65) Prior Publication Data

US 2018/0168883 A1    Jun. 21, 2018

Related U.S. Application Data

(60) Division of application No. 14/800,822, filed on Jul. 16, 2015, now abandoned, which is a continuation of
(Continued)

(51) Int. Cl.
    A61F 13/15      (2006.01)
    A61F 13/514     (2006.01)
    (Continued)

(52) U.S. Cl.
    CPC .. *A61F 13/15699* (2013.01); *A61F 13/15682* (2013.01); *A61F 13/15739* (2013.01);
    (Continued)

(58) Field of Classification Search
    None
    See application file for complete search history.

(56) References Cited

U.S. PATENT DOCUMENTS 5,143,679 A     9/1992  Weber et al.
5,376,198 A  * 12/1994  Fahrenkrug ....... A61F 13/15203
                                                  156/163
(Continued)

FOREIGN PATENT DOCUMENTS

CA    2578730 C    4/2006
EP    0274752 A2   7/1988
(Continued)

OTHER PUBLICATIONS

Office Action (Communication) dated Jan. 31, 2019, by the European Patent Office in corresponding European Patent Application No. 04788541.3. (5 pages).
(Continued)

*Primary Examiner* — Jeffry H Aftergut
(74) *Attorney, Agent, or Firm* — Buchanan Ingersoll & Rooney PC

(57) ABSTRACT

A method for production of disposable hygienic absorbent articles, the method comprising advancing in a first direction a continuous length of a substantially homogeneous elastic laminate web having a maximum elastic extensibility in the first direction of at least 40% under a peak load $F_p$; maintaining said substantially homogeneous elastic laminate web under a tensioning load $F_t$ in the first direction during the advancing, the tensioning load $F_t$ satisfying the condition: $0.03 F_p \leq F_t \leq 0.25 F_p$; attaching individual absorbent cores to the substantially homogeneous elastic laminate web while maintaining said substantially homogeneous elastic laminate web under the tensioning load $F_t$; and severing the substan-
(Continued)

tially homogenous elastic laminate web into individual disposable hygienic absorbent articles.

13 Claims, 4 Drawing Sheets

Related U.S. Application Data application No. 11/658,539, filed as application No. PCT/SE2004/001384 on Sep. 29, 2004, now Pat. No. 9,114,041.

(51) Int. Cl.
  *B32B 37/22* (2006.01)
  *B32B 38/00* (2006.01)
  *B32B 37/02* (2006.01)
  *B32B 37/12* (2006.01)

(52) U.S. Cl.
  CPC .. *A61F 13/15747* (2013.01); *A61F 13/51401* (2013.01); *A61F 13/51464* (2013.01); *B32B 37/22* (2013.01); *B32B 38/0004* (2013.01); *B32B 38/0012* (2013.01); *B32B 38/1875* (2013.01); *B32B 37/02* (2013.01); *B32B 37/12* (2013.01); *B32B 2305/34* (2013.01); *B32B 2307/726* (2013.01); *B32B 2555/02* (2013.01); *Y10T 156/1084* (2015.01)

(56) References Cited

U.S. PATENT DOCUMENTS

| | | | |
|---|---|---|---|
| 5,422,172 A | | 6/1995 | Wu |
| 5,543,206 A | | 8/1996 | Austin et al. |
| 5,964,390 A | * | 10/1999 | Borresen ............. B65H 23/025 226/118.2 |
| 6,092,002 A | | 7/2000 | Kastman et al. |
| 6,149,637 A | | 11/2000 | Allen et al. |
| 6,313,372 B1 | | 11/2001 | Suzuki |
| 6,472,084 B1 | | 10/2002 | Middlesworth et al. |
| 6,500,377 B1 | * | 12/2002 | Schneider ......... A61F 13/15707 100/224 |
| 6,720,279 B2 | | 4/2004 | Cree et al. |
| 6,732,778 B1 | | 5/2004 | Machida et al. |
| 6,942,748 B2 | | 9/2005 | Cree et al. |
| 2003/0017345 A1 | | 1/2003 | Middlesworth et al. |
| 2003/0105446 A1 | * | 6/2003 | Hutson ............... A61F 13/4902 604/385.22 |
| 2004/0102754 A1 | * | 5/2004 | Morman ........... A61F 13/15203 604/385.24 |
| 2010/0298798 A1 | | 11/2010 | Lakso |

FOREIGN PATENT DOCUMENTS

| | | | |
|---|---|---|---|
| EP | 0 650 714 A1 | | 5/1995 |
| EP | 0685586 A2 | * | 12/1995 |
| EP | 0685586 A2 | | 12/1995 |
| EP | 0714351 B1 | | 12/1998 |
| EP | 1 199 057 A1 | | 4/2002 |
| JP | 07-252762 | | 10/1995 |
| JP | 2000-509672 T | | 8/2000 |
| JP | 2001-29385 A | | 2/2001 |
| JP | 2001-526937 T | | 12/2001 |
| JP | 2002-512566 A | | 4/2002 |
| JP | 2004-96356 A | * | 4/2004 |
| JP | 2004-098356 A | | 4/2004 |
| WO | 95/18589 A1 | | 7/1995 |
| WO | 98/37266 | | 8/1997 |
| WO | 98/21035 | | 5/1998 |
| WO | 99/33427 | | 7/1999 |
| WO | 01/56525 A1 | | 8/2001 |
| WO | 03/070140 A1 | | 8/2003 |
| WO | WO-03/070140 A1 | * | 8/2003 |
| WO | 2010/050867 A1 | | 5/2010 |

OTHER PUBLICATIONS

International Search Report dated Apr. 12, 2005.
English language translation of an Office Action dated Nov. 4, 2009 in corresponding Japanese Patent Application No. 2007-533421.
Machine Translation of Japanese Patent 2004-98356, date unknown.
Notice of Opposition to an European Patent filed by Kimberly-Clark Worldwide, Inc. in corresponding European Patent Application No. EP 04788541.3, now EP Patent No. EP 1793783, on Apr. 11, 2013.
Notice of Opposition to an European Patent filed by The Proctor & Gamble Company in corresponding European Patent Application No. EP 04788541.3, now EP Patent No. EP 1793783, on Apr. 2, 2013.
American Society for Testing and Materials (ASTN D882), "Standard Test Method for Tensile Properties of Thin Plastic Sheeting," American Society for Testing and Materials, 1998.
Rolsum, David R., "The Mechanics of Web Handling," TAPPI Press, 1998, ISBN: 0-89852-346-X, pp. 49-52.
Rolsum David R., "The Mechanics of Web Handling (table of contents)," TAPPI Press, 1998, ISBN: 0-89852-346-X, pp. 1-4.
Rolsum, David R., "The Mechanics of Rollers," USA: TAPPI Press, 1998, ISBN: 0-89852-313-3, p. 12.
Damour, J., "The Mechanics of tension control," Feb. 26, 2004, Available from [http://www.converteraccessory.com/ppt/PDF/tc_tech.pdf], pp. 1, 21 and 69.
Ground of Appeal issued in corresponding European Patent No. 1793783, dated Apr. 9, 20015.
Opponent's Appeal submitted to European Patent Office in European Patent No. 1793783; dated Apr. 2, 2015; 8 pages.
Opponent's Appeal submitted to European Patent Office corresponding to European Patent No. 1793783; dated Mar. 25, 2015; 4 pages.

* cited by examiner

METHOD FOR PRODUCTION OF DISPOSABLE ABSORBENT ARTICLES

The present application is a divisional application of U.S. Ser. No. 14/800,822, filed on Jul. 16, 2015, which is a continuation of U.S. Ser. No. 11/658,539, filed on Jan. 25, 2007, which is a national stage application of PCT/SE2004/001384, filed on Sep. 29, 2004. The entire contents of U.S. Ser. No. 14/800,822; U.S. Ser. No. 11/658,539 and PCT/SE2004/001384 are incorporated herein by reference.

TECHNICAL FIELD

The present invention relates to a method for production of disposable hygienic absorbent articles such as pants-type absorbent articles.

BACKGROUND OF THE INVENTION

In order to improve comfort and fit, disposable hygienic articles, and particularly those which are intended to be worn around the waist of a user, are commonly provided with elastic components in selected regions of the article. In a pants-type absorbent article, i.e. an article which is pulled on in the same manner as a traditional pair of pants, the selected regions comprise the waist opening and the leg openings. Conventionally, the elastic components used in these regions are in the form of elastic threads or bands which are secured to a substrate, e.g. the outer cover of the article, in a stretched state under a tensioning force. When the tensioning force is released, the elastic components contract and thereby gather the substrate to which they are secured. In this manner, an otherwise substantially inelastic material web can be provided with elastic properties.

The above-described manner of providing elasticised regions on an absorbent article suffers from several drawbacks. For example, securing the elastic components to a running material web in a continuous process is relatively complicated. The elastic components are generally secured to the material web with adhesive, for example hot-melt adhesive or thermosetting adhesive. To ensure that the elastic components do not release from the material web during the production process, it is necessary to ensure that the elastic components bear against the material web until the adhesive has set, dried or hardened. Problems may also arise in synchronizing the tensioning of the different elastic components and in achieving uniform tensioning of the different elastic components independently of the speed of the running web material. Since the extent of elasticity of the thus elasticised material web is directly proportional to the degree to which the elastic components are tensioned, typically 100%, when attached to the material web, during production the articles occupy an area which is substantially greater than that occupied by the finished articles in a relaxed state. This implies that the production facility takes up an undesirably large area. In addition, the production equipment has to be dimensioned to accommodate the tensioning force. A further difficulty is that of handling the finished articles once they have been severed from the running material web, since the articles assume an irregular three-dimensional shape as soon as the tensioning of the elastic components ceases. Folding and packaging of the finished articles have additionally proven to be very difficult steps because of their creased and three-dimensional shape.

Although such elasticised disposable absorbent articles may provide satisfactory comfort and fit, the thus gathered material web can impart a bulky, creased appearance to the article. This implies that it may be difficult to conceal the article under normal clothing. This is particularly problematic for adult users of disposable absorbent pants.

To overcome at least some of these drawbacks, rather than using an elasticised material in disposable absorbent articles, it has been proposed to make at least some regions of disposable absorbent articles of elastic material per se, for example an elastic nonwoven or elastic laminate. By using such material, there is no need to secure a tensioned elastic component to a gatherable substrate. As such, theoretically at least, it is possible to manufacture disposable absorbent articles in a process in which the constituent elastic components are substantially unstretched. Indeed, in WO-A-03/070140 it is proposed to stretch the elastic material web during production to a maximum of 5%.

The present inventors have found that, in order to ensure accurate control of the elastic material web during production, it is necessary to subject the web to a certain minimum tensioning load. On the other hand, to enjoy as many as possible of the advantages that, at least theoretically, are available using an elastic material web vis-à-vis an elasticised web, it is important that the tensioning load be significantly less than the load to attain maximum elastic extensibility of the elastic material web.

OBJECTS AND SUMMARY

It is therefore an object of the invention to provide a method of production of disposable hygienic absorbent articles which permits efficient production of the articles.

According to one method, a disposable hygienic absorbent article is produced in a process in which an elastic material web is a substantially homogenous elastic laminate web having a maximum elastic extensibility in a first direction of at least 40%, preferably at least 60%, and most preferably at least 80%, under a peak load $F_p$. The elastic laminate web is advanced in a direction of travel corresponding to the first direction while being maintained under a tensioning load $F_t$ satisfying the condition: $0.03 F_p \leq F_t \leq 0.25 F_p$.

For the purposes of this disclosure, an elastic laminate web is to be regarded as substantially homogenous if the properties of the web at any two sections of the web are essentially the same in the same direction.

Elastic extensibility here refers to the lengthening of the elastic laminate web in the direction of applied load which the web permits without plastically deforming or rupturing. For a material to be deemed to be elastically extensible it must also strive to recover its original length once the tensioning load is removed. For present purposes, a laminate web is deemed to be elastically extensible if it can be extended in at least one direction to at least 130% of its initial length, and will revert to at most 120%, preferably no more than 110%, of its original length upon removal of the tensioning load, while still meeting the requirement of maximum elastic extensibility outlined above.

Due to the non-linear load/elongation property of elastic laminate webs caused by the inter-engagement of fibres of the less elastic layer or layers of the laminate, the %-elongation per unit load decreases at higher values of elongation. By selecting the tensioning load $F_t$ so as to satisfy the condition $0.03 F_p \leq F_t \leq 0.25 F_p$, adequate extension of the web is assured at the same time that the production equipment is not subjected to unnecessarily large forces.

Under certain circumstances, it may be preferable to increase the elongation of the laminate during production. As such, in a preferred embodiment, the tensioning load $F_t$ may be selected so as to satisfy the condition $0.05 F_p \leq F_t \leq 0.25 F_p$. Similarly, where it is desirable to keep the load on the laminate as low as possible, $F_t$ may be selected so as to satisfy the condition $0.03 F_p \leq F_t \leq 0.20 F_p$. In a further preferred embodiment, $F_t$ may be selected so as to satisfy the condition $0.05 F_p \leq F_t \leq 0.20 F_p$.

Preferably, the elastic laminate web comprises at least one nonwoven layer affixed to a film layer. The film layer is preferably an apertured three-layer PE/styrene-based film/PE elastomeric film.

BRIEF DESCRIPTION OF DRAWINGS

Embodiments of the invention will be described in the following in greater detail by way of example only and with reference to the attached drawings, in which.

DETAILED DESCRIPTION OF PREFERRED EMBODIMENTS

Figure 1:
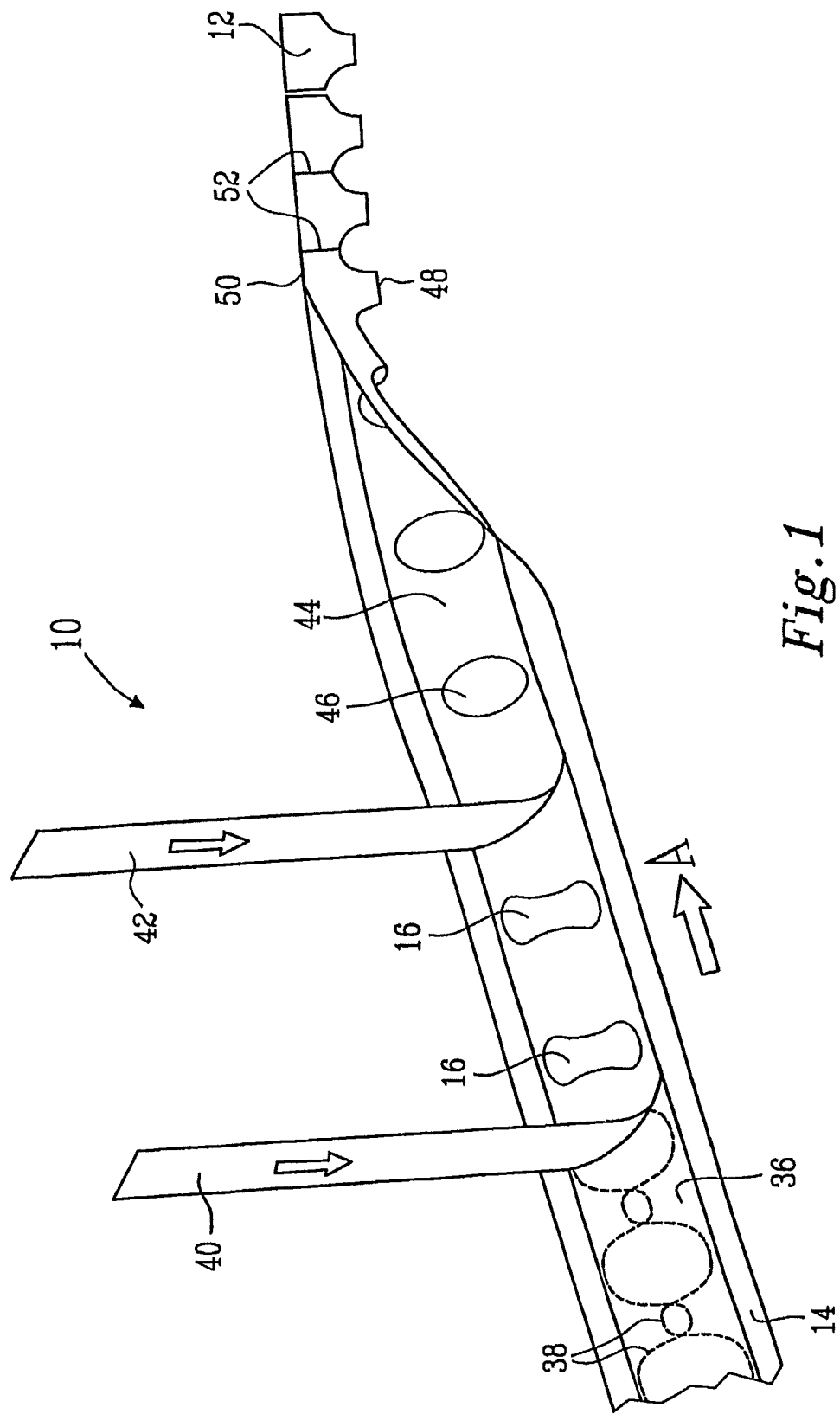
FIG. 1 is a schematic perspective view of a length of a production line for the production of a disposable hygienic absorbent article in accordance with an embodiment of the present invention.

In FIG. 1, reference numeral 10 generally denotes length of a production line for the production of a disposable hygienic absorbent article 12. In the present example, the absorbent article is a pull-up pants-type diaper.

The various components of the absorbent article are united on a (not shown) continuous conveyor belt running in a direction of travel denoted by arrow A. In the broadest form of the invention, a continuous length of a substantially homogenous elastic laminate web 14 is placed on the conveyor belt and maintained under a tensioning load $F_t$. The elastic laminate web has a maximum extensibility in a first direction corresponding to the direction of travel denoted by arrow A of at least 40%, preferably at least 60%, and most preferably at least 80%, under a peak load $F_p$. The continuous length of the elastic laminate web 14 is advanced in the direction of travel A to a station at which individual absorbent cores 16 are attached to the continuous length of the elastic laminate web 14 at spaced intervals. Individual articles 12, in this case pull-up pants-type diapers, are thereafter formed from the thus assembled individual absorbent cores 16 and the continuous length of the elastic laminate web.

The continuous length of the elastic laminate web 14 is maintained under a tensioning load $F_t$ in the direction of travel during the advancing, with the tensioning load $F_t$ satisfying the condition: $0.03 F_p \leq F_t \leq 0.25 F_p$.

In order to carry out the above described method, it is necessary to determine the peak load $F_p$, i.e. the load under which the elastic laminate web displays elastic extensibility. The peak load is determined using the ASTM D 882 tensile strength test method. The tensile strength and elongation of a well-defined test piece is tested by means of a tensile tester.
Apparatus: Instron 4301
Tensile tester connected to a computer
Crosshead speed: 500 mm/min
Clamp distance: 50 mm Sample preparation: Test samples are cut from the entire width of the material. The width of the sample shall be 25.4 mm and the length at least 50 mm longer than the clamp distance if possible. It is of importance that the edges of the sample are even and without break notches. The samples are conditioned for at least 4 h in 50% RH±5% RH and 23° C.±2° C. before testing.

Procedure: The tensile tester is calibrated according to the apparatus instructions and set to zero. The sample is mounted and it is ensured that it is not obliquely or unevenly fastened. The material is prevented from slipping by using clamps covered with galloon or similar material. The tensile tester is started, and stopped after the material has broken (if not automatically controlled). Measurements resulting from premature failures (i.e. the sample breaks at the clamp, or is damaged during preparation) are ignored if possible.

The following results are expressed by the tensile tester/computer:
Maximum force, N/25.4 mm
Elongation at maximum force, %
Break force, N/25.4 mm
Elongation at break force, %
Knee point, N/%

Figure 2:
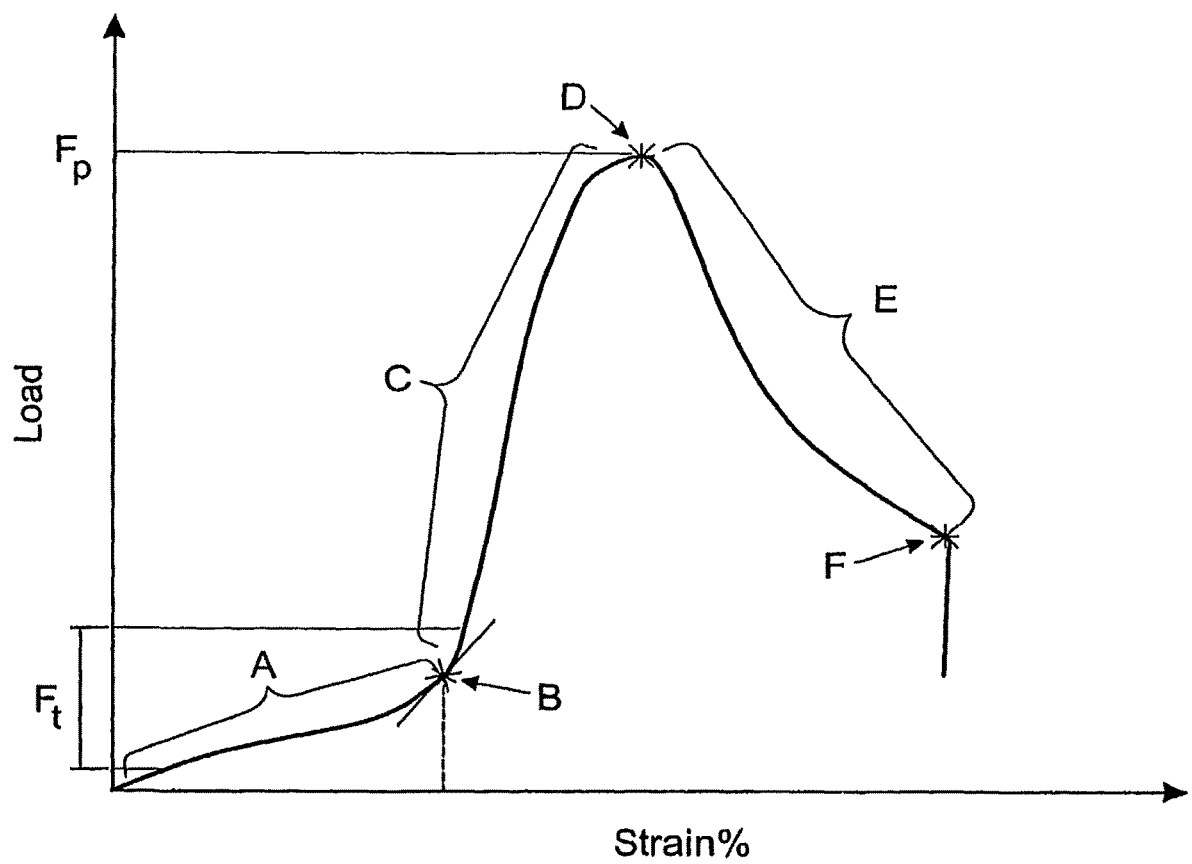
FIG. 2 is a schematic graphic representation showing load vs. strain for an elastic laminate.

FIG. 2 is a schematic representation of the behaviour of an elastic laminate web for use in the method according to the present invention under stretching at a constant strain. The laminate web comprises 25 gsm Sofspan NW from BBA on both sides of a 40 gsm apertured elastic film, where one face is glue-laminated with approximately 5 gsm glue.

From zero strain, the elastic laminate web exhibits substantially elastic behaviour in region (A) up to around a "knee point" (B), after which, the load increases rapidly through region (C). The knee point (B) is defined as the first point on the load-strain curve at which the gradient becomes greater than 0.3N/%. The laminate web shown is elastic up to about 80% strain. The applied load eventually reaches a maximum (the "peak load") at point (D), at which the gradient of the load-strain curve is zero. The load then drops through region (E) as the material fails. Complete failure of the laminate web occurs at point (F).

The peak load $F_p$ is the applied load at point D. In the embodiment of the present invention, the elastic laminate web is maintained under a tensioning load $F_t$ which satisfies the condition: $0.03 F_p \leq F_t \leq 0.25 F_p$.

Figure 3:
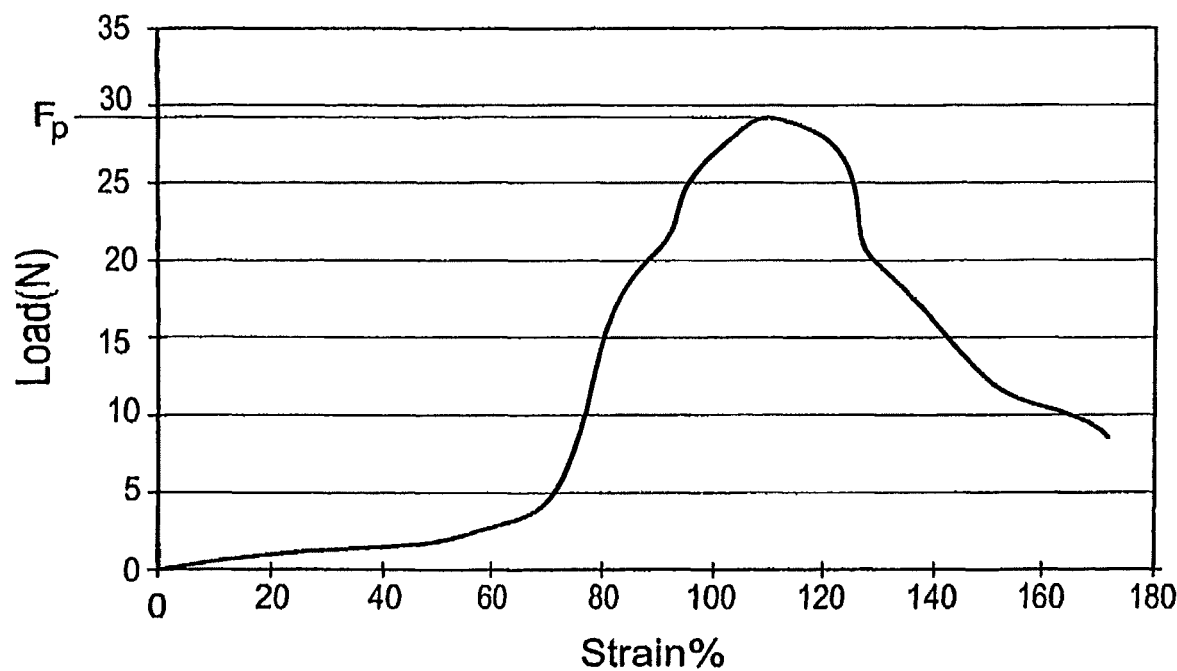
FIG. 3 is a graph showing load vs. strain for an elastic laminate comprising 25 gsm nonwoven material.
Figure 4:
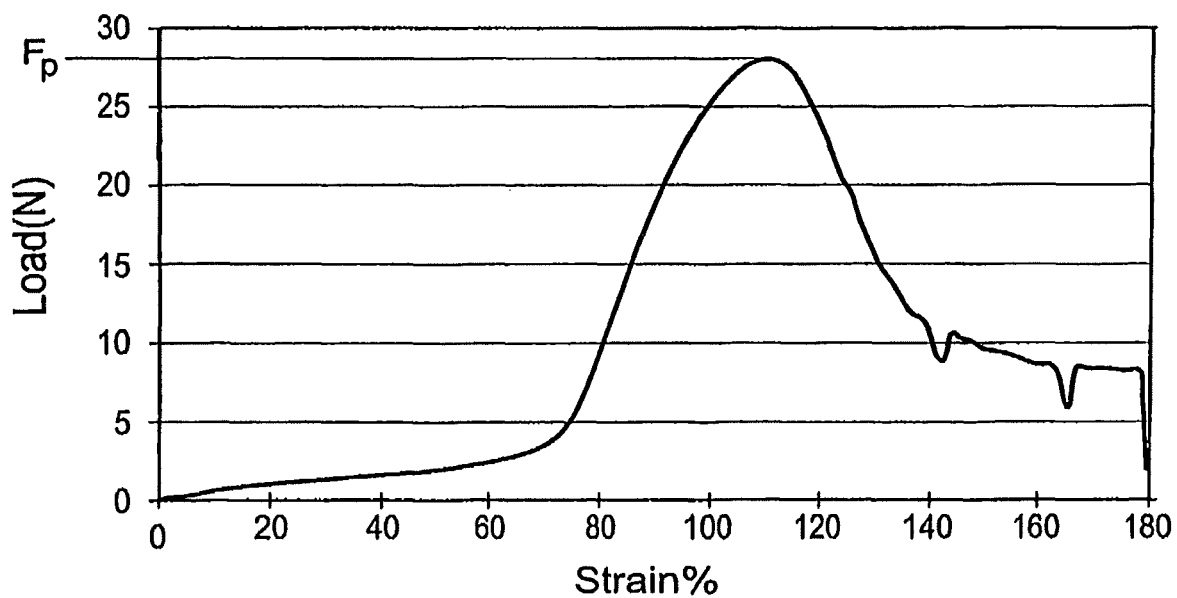
FIG. 4 is a graph showing load vs. strain for an elastic laminate comprising 20 gsm nonwoven material.
Figure 5:
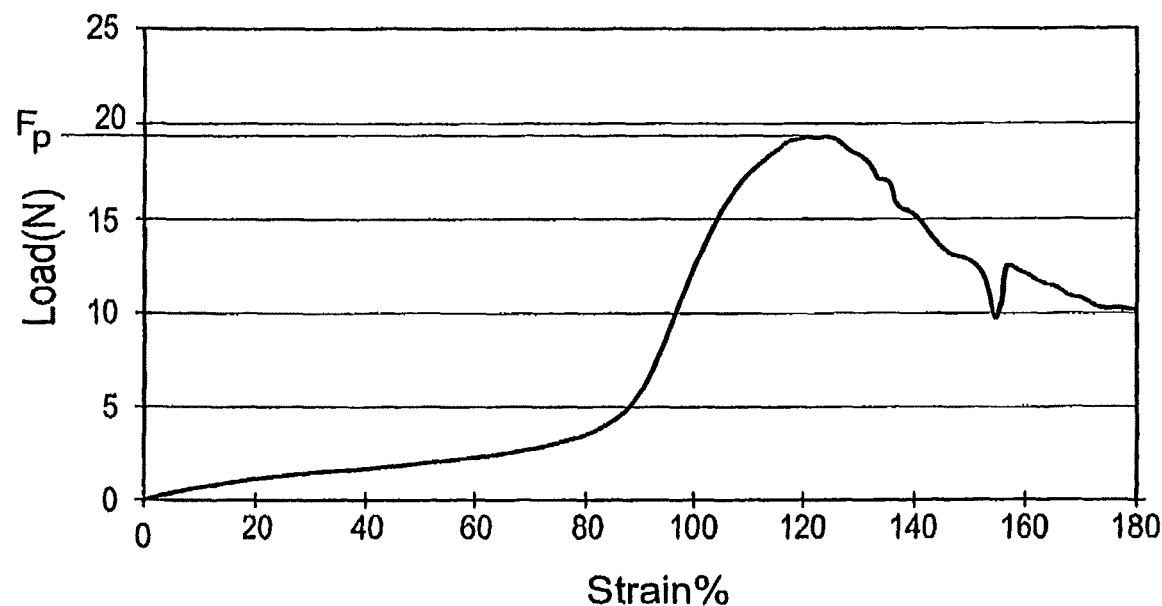
FIG. 5 is a graph showing load vs. strain for an elastic laminate comprising 18 gsm nonwoven material.

FIGS. 3 to 5 show the actual behaviour of elastic laminate webs having a 40 gsm apertured elastic film, though glue-laminated with approximately 3 gsm glue to Sofspan NW of different basis weights. Thus, in FIG. 3 the basis weight of the nowwoven webs is 25 gsm, in FIG. 4 it is 20 gsm and in FIG. 5 it is 18 gsm. In all cases, the "knee point" (B) lies within the range $0.03 F_p \leq F_t \leq 0.25 F_p$.

Under certain circumstances, it may be preferable to increase the elongation of the laminate during production. As such, in a preferred embodiment, the tensioning load $F_t$ may be selected so as to satisfy the condition $0.05 F_p \leq F_t \leq 0.25 F_p$. Similarly, where it is desirable to keep the load on the laminate as low as possible, $F_t$ may be selected so as to satisfy the condition $0.03 F_p \leq F_t \leq 0.20 F_p$. In a further preferred embodiment, $F_t$ may be selected so as to satisfy the condition $0.05 F_p \leq F_t \leq 0.20 F_p$.

Figure 6:
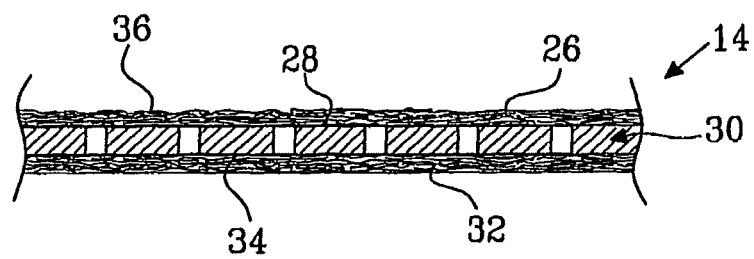
FIG. 6 is a cross-sectional view through an elastic laminate web for use in an embodiment of the present invention.

FIG. 6 is a cross-section through an elastic laminate web 14 for use in an embodiment of the present invention. The elastic laminate web comprises a first nonwoven layer 26 affixed to a first surface 28 of a film layer 30. Advantageously, the elastic laminate web further comprises a second nonwoven layer 32 affixed to a second surface 34 of the film layer 30.

Preferably, the film layer comprises an elastic film having a basis weight from about 20 g/m² to about 100 g/m², preferably between 20 and 60 g/m². The film layer may be selected from the group consisting of low crystallinity polyethylenes, metallocene-catalyzed low crystallinity polyethylene, ethylene vinyl acetate copolymers (EVA), polyurethane, polyisoprene, butadiene-styrene copolymers, styrene block polymers such as styrene/isoprene/styrene (SIS), styrene/butadiene/styrene (SBS), styrene/ethylene-butadiene/styrene (SEBS) block copolymer and blends thereof.

To increase the breathability of the elastic laminate web, the film layer 30 may be provided with apertures 37. In a preferred embodiment, the film is an apertured three-layer PE/styrene-based film/PE elastomeric film.

Each of the first and second nonwoven layers may have a basis weight of from about 10 g/m² to about 40 g/m², preferably from about 12 g/m² to about 30 g/m², most preferably from about 15 g/m² to about 25 g/m², and may comprise a spunbond or carded material selected from the group consisting of: polypropylene, polyethylene, polyester and other polyolefin homopolymers and copolymers.

In order to provide the individual articles 12 with desirable properties, the basic production method outlined above may be complemented by one or more of the following steps.

In the production of a pants-type diaper, adhesive 36 may be applied, for example by spraying or coating, to the elastic laminate web 14, after which elastic members 38 in the form of continuous elastic bands or threads are secured in a curved pattern across the laminate web. These elastic members 38 will form elasticised leg openings in the completed article 12. Alternatively, the adhesive may be applied directly to the elastic members themselves.

A second material web 40 of liquid barrier material, such as an elastic plastic film, may thereafter be applied over the elastic laminate web 14 and the elastic members 38. The second material web may be provided with adhesive on its surface facing the first web 14 to ensure its adequate adhesion thereto.

In the illustrated embodiment a third material web 42 is placed over the elastic laminate web 14 and the second material web 40 and secured over the absorbent cores 16. The third elastic material web will constitute the topsheet of the completed absorbent article. As such, it can consist of a nonwoven material, e g spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and intended to be readily penetrated by body fluid, e.g. urine or menstrual fluid. Advantageously, the third material web will have elastic properties. Before the third material web is applied to the second material web, the third elastic web may be coated with an adhesive on its surface directed towards the second material web.

In an alternative production method, the second material web 40 of liquid barrier material may be omitted. Instead, nonwoven material may be placed over the elastic members 38. Liquid barrier material may then be incorporated in an absorbent packet comprising a plastic film, an absorbent core and a nowoven surface layer. Although in FIG. 1 the elastic members 38 as laid out on the elastic laminate web comprise crotch elastic, it is to be understood that the crotch elastic may be incorporated in the thus-described absorbent packet instead.

The above-described assembly of components forms a production web 44. Leg openings 46 are cut out from the production web and the production web is then folded double in the production direction so that a fold edge 48 and an open edge 50 are formed. The folded production web 44 is then welded intermittently transverse to the production direction along weld lines 52 extending from the open edge 50 to the edge at each leg opening 46. The welded production web 44 is then divided by being severed along each weld line 52 so that individual pants-type diapers 12 are separated from the production web 44. The individual diapers can then be subjected to further processing steps such as folding and packing.

The elastic laminate web 14 of the thus-produced pants-type diapers 12 constitutes the outer cover of the diapers. In a similar manner, the elastic laminate web may also constitute the outer cover of many types of disposable hygienic absorbent articles, such as conventional diapers, incontinence garments, sanitary napkins and panty liners. It is to be understood that the elastic laminate web 14 need not cover the entire outer surface of such articles. Instead, in certain circumstances it may be desirable to have a non-elastic region of the outer cover. Thus, for example, the crotch region of a diaper may have an outer cover region which is constituted by a strip of non-elastic nonwoven material bounded on either side by an elastic laminate web. In this manner, front and rear panels of the diaper will enjoy elastic properties.

What is claimed is:

1. A method for production of disposable hygienic absorbent articles, the method comprising:
   advancing in a first direction a continuous length of a substantially homogeneous elastic laminate web having a maximum elastic extensibility in the first direction of at least 40% under a peak load $F_p$;
   maintaining said substantially homogeneous elastic laminate web under a tensioning load $F_t$ in the first direction during the advancing, the tensioning load $F_t$ satisfying the condition: $0.03\ F_p \leq F_t \leq 0.25\ F_p$;
   attaching individual absorbent cores to the substantially homogeneous elastic laminate web while maintaining said substantially homogeneous elastic laminate web under the tensioning load $F_t$; and
   severing the substantially homogenous elastic laminate web into individual disposable hygienic absorbent articles.

2. The method as claimed in claim 1, further comprising welding said substantially homogeneous elastic laminate web to define weld lines intermittently transverse to the first direction.

3. The method as claimed in claim 1, wherein:
   said substantially homogenous elastic laminate web includes two layers having respective levels of elasticity different from one another, and
   said substantially homogenous elastic laminate web exhibits a non-linear load-strain curve relationship.

4. The method as claimed in claim 1, wherein the individual disposable hygienic absorbent articles are pull-up pant diapers.

5. The method as claimed in claim 1, wherein the individual absorbent cores include a plastic film, an absorbent core, and a nonwoven surface layer.

6. The method as claimed in claim 5, wherein the individual absorbent cores further include a crotch elastic.

7. The method as claimed in claim 1, wherein the absorbent cores are attached to the substantially homogenous elastic web and the substantially homogenous elastic web is severed such that the substantially homogenous elastic web is arranged on a side of the absorbent cores such that the substantially homogenous elastic web forms an outer cover for the individual disposable hygienic absorbent articles and the substantially homogeneous elastic laminate web does not cover an entire outer surface of the individual disposable hygienic absorbent articles.

8. The method as claimed in claim 7, wherein the absorbent cores are attached to the substantially homogenous elastic web and the substantially homogenous elastic web is severed such that the substantially homogenous elastic web is arranged on a side of the absorbent cores such that the substantially homogenous elastic web forms an outer cover for the individual disposable hygienic absorbent articles and the outer cover of the individual disposable hygienic absorbent articles has a non-elastic region.

9. The method as claimed in claim 1, wherein the absorbent cores are attached to the substantially homogenous elastic web and the substantially homogenous elastic web is severed such that the substantially homogenous elastic web is arranged on a side of the absorbent cores such that the substantially homogenous elastic web forms an outer cover for the individual disposable hygienic absorbent articles.

10. The method as claimed in claim 1, wherein:
the substantially homogenous elastic laminate web comprises at least one nonwoven layer affixed to a film layer.

11. The method as claimed in claim 10, wherein:
said substantially homogenous elastic laminate web exhibits a non-linear load-strain curve relationship.

12. The method as claimed in claim 1, wherein:
said substantially homogenous elastic laminate web exhibits a non-linear load-strain curve relationship.

13. The method as claimed in claim 1, wherein:
the tensioning load $F_t$ satisfies the condition: $0.05\ F_p \le F_t \le 0.25\ F_p$.

* * * * *